United States Patent [19]

Gluzek et al.

[11] Patent Number: 4,921,879

[45] Date of Patent: May 1, 1990

[54] NOVEL BICYCLIC AMINE CATALYSTS

[75] Inventors: Karl-Heniz Gluzek, Alpen; Heiko Humbert, Hamburg, both of Fed. Rep. of Germany

[73] Assignee: Duetshe Texaco Aktiengesellshaft, Hamburg, Fed. Rep. of Germany

[21] Appl. No.: 378,463

[22] Filed: Jul. 13, 1989

Related U.S. Application Data

[62] Division of Ser. No. 165,855, Mar. 9, 1988, abandoned.

[30] Foreign Application Priority Data

Mar. 12, 1987 [DE] Fed. Rep. of Germany ....... 3707911

[51] Int. Cl.[5] ........................................ C08G 18/20

[52] U.S. Cl. ........................................ 521/129; 528/54

[58] Field of Search ........................... 528/54; 521/129

[56] References Cited

U.S. PATENT DOCUMENTS

| | | | |
|---|---|---|---|
| 3,036,021 | 5/1962 | Trescher et al. | 528/54 |
| 3,169,972 | 2/1965 | Paquette | 521/129 |
| 3,483,224 | 12/1969 | Fitzpatric | 502/167 |
| 4,028,364 | 6/1977 | Adelstein | 546/112 |
| 4,065,497 | 12/1977 | Grier et al. | 564/270 |
| 4,079,141 | 3/1978 | Ong et al. | 546/112 |
| 4,397,857 | 8/1983 | Vincent et al. | 546/112 |
| 4,405,787 | 9/1983 | Gaitanopoulos et al. | 546/112 |
| 4,617,154 | 10/1986 | Green | 502/167 |

OTHER PUBLICATIONS

Larsen et al., "Aza Diels-Alder Reactions in Aqueous Solution: Cyclocondensation of Dienes with Simple Iminium Salts Generated under Mannich Conditions", J. Am. Chem. Soc., 107, 1768-1769, 1985.

Chem.-Abstract, 103:6713b, Jun. 20, 1984.

*Primary Examiner*—Maurice J. Welsh
*Assistant Examiner*—Rabon Sergent
*Attorney, Agent, or Firm*—Thomas H. Whaley

[57] ABSTRACT

New catalysts are made available for the production of polyurethane and polyepoxide resins being derivates of 2-azabicyclo[2.2.2]hept-5-enes and 2-azabicyclo[2.2.1-]heptanes substituted in 2- and optionally in 3-position. Also provided is a process for preparing same by reacting cyclopentadiene with salts of strong acids of ammonia or of primary amines and aldehydes and, optionally, by subsequent catalytic hydrogenation of the reaction product.

25 Claims, No Drawings

NOVEL BICYCLIC AMINE CATALYSTS

This is a division of application Ser. No. 165,855, filed March 9, 1988 now abandoned.

BACKGROUND OF THE INVENTION

The present invention relates to the preparation of substituted 2-azabicyclo[2.2.1]hept-5-enes by reacting cyclopentadiene with ammonium salts or the salts of primary amines and carbonyl compounds to form the salts of 2-azabicyclo[2.2.1]hept-5-ene derivatives, neutralization of the salts and, possibly, hydrogenation of the bases to form derivatives of the 2-azabicyclo[2.2.1-]heptane, as well as to the application of the products obtained by this process as amine catalysts.

It is known that N-alkyl-2-azabicyclo[2.2.1]heptanes can be prepared by Hoffman-Loffler-Freytag reaction starting from N-alkyl-aminomethylcyclopentane compounds, the starting materials being synthesized in several steps from cyclopentane carboxylic acid and a primary amine, see P. G. Gassmann and D. C. Heckert, Tetrahedron 21, 2725 (1965). Thus, for instance, the N-ethyl-2-azabicyclo[2.2.1]heptane can be prepared in a total yield of 24%. As a result of the low total yield and the high price of cyclopentane carboxylic acid used as a starting material, the manufacturing procedure described has not been accepted in the art.

Furthermore, it is known that 2-azabicyclo[2.2.1-]hept-5-ene derivatives substituted on the nitrogen can be prepared by reacting iminium salts with cyclopentadiene, see S. D. Larsen and P. A. Grieco, J. Am. Chem. Soc. 107, 1768 (1985). S. D. Larsen and P. A. Grieco performed the reaction at room temperature or at a slightly higher temperature in a water/cyclopentadiene two-phase system using aminohydrochlorider and formalin at an excess of 30–40 mole %.

Linear, mono-, or bicyclic amines are commonly used in the art as catalysts for the production of polyurethanes. Thus, it is the object of the invention to prepare new bicyclic amines which are suitable as catalysts and can be synthesized from technically easily accessible and low-priced raw materials.

Accordingly, the problem of the prior art is resolved by providing as catalysts the compounds of the present invention.

SUMMARY OF THE INVENTION

This invention provides a catalyst which may be used alone or in a mixture to produce polyurethanes and polyepoxide resins. The catalyst comprises:

substituted 2-azabicyclo[2.2.1]hept-5-ene derivatives of the formula

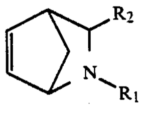

and of the corresponding 2-azabicyclo[2.2.1]heptane derivatives of the formula

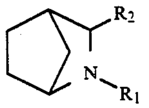

wherein $R_1$ is a $(C_1-C_8)$alkyl group, a $(C_2-C_8)$ alkenyl group, a $(C_5-C_9)$cycloalkyl or alkylcycloalkyl group, benzyl or a $(C_3-C_{10})$ alkylbenzyl group with one or more of the heteroatoms N, O, or S;

$-(CH_2)_a-P$, $(-CH_2)_b-T-(CH_2)_c-U$, or $-(CH_2)_D-V-(CH_2)_e-W-(CH_2)_f-X$ wherein a through f are 2, 3, or 4, P, U, X are each the same or different and are OH, O—acyl, N—acyl, N—$(C_1-C_4)$alkyl, N—di—$(C_1-C_4)$alkyl, or are 2-azabicyclo—[2.2.1]heptyl, T, V, W are each equal or different and are O, NH, or N—$(C_1-C_4)$alkyl; and $R_2$ is hydrogen or a $(C_1-C_4)$alkyl group.

DETAILED DESCRIPTION OF THE INVENTION

The 2-azabicyclo[2.2.1]hept-5-enes and 2-azabicyclo[2.2.1]heptanes are prepared according to syntheses of organic chemistry known as such. The raw materials are primary amines or the salts thereof with strong acids, carbonyl compounds, and cyclopentadiene. Formaldehyde is the preferred carbonyl component.

The present process is performed in two synthesis steps:

The first step comprises the preparation of the 2-azabicyclo[2.2.1]hept-5-ene derivative. To this end a primary amine is neutralized with a strong mineral acid, such as hydrochloric acid, sulfuric acid, phosphoric acid, or a strong organic acid, e.g., p-toluene sulfonic acid, or mixtures thereof, is reacted with a carbonyl compound, particularly formalin, to form the iminium salt, and - after addition of the cyclopentadiene-, is converted into the 2-azabicyclo[2.2.1]hept-5-ene derivative in the two-phase system, particularly at 40° to 45° C.

The reaction only takes place in the acidic pH-range, preferably in a pH-range of 2 to 6, particularly of 2 to 3.

Ammonium salts like ammonium chloride give only moderate yields, because formalin has an alkylating effect such that a mixture of 2-azabicyclo[2.2.1]hept-5-ene and N-methyl-2-azabicyclo[2.2.1]hept-5-ene is formed which is difficult to separate by distillation.

By addition of strong bases, such as alkali hydroxides, alkaline earth oxides, alkaline earth hydroxides, or organic bases the amine is set free from the salt of the 2-azabicyclo[2.2.]hept-5-ene derivative.

In the second synthesis step the 2-azabicyclo[2.2.1-]hept-5-ene is hydrogenated. For this operation it is not necessary to use the pure 2-azabicyclo[2.2.1]hept-5-ene derivative. Instead thereof the crude product that may yet contain water can directly be hydrogenated in the known way in the presence of a catalyst.

The hydrogenation is usually performed under pressure in the presence of a noble metal catalyst, particularly of the platinum group, and preferably in the presence of palladium. This operation may also be performed at elevated temperature.

For the hydrogenation either the free bases or directly the salts obtained as a solution can be used. Preferably, the free bases are hydrogenated. The process can be performed batchwise or continuously.

Both the 2-azabicyclo[2.2.1]hept-5-ene and the 2-azabicyclo[2.2.1]heptane are solid materials, see A. Hessing and W. Herdering, Chem. Ber. 116, 1081-1096 (1983). All the other compounds prepared are liquids which can be distilled under vacuum.

The 2-azabicyclo[2.2.1]heptane derivatives are thermally more stable than the initial 2-azabicyclo[2.2.1-]hept-5-ene derivatives which, in inversion of the formulation, partly decompose into the starting materials. The volatile compounds are characterized by an amine-like odor; high-boiling 2-azabicyclo[2.2.1]heptane derivatives are virtually odorless.

The 2-azabicyclo[2.2.1]heptane derivatives prepared according to the described process can be further varied provided the side chain $R_1$ has OH, halogen, or NH groups. For instance, the OH group of the N-(2-hydroxy-ethyl-) or the N(2-hydroxyethoxyethyl)-2-azabicyclo[2.2.1]heptane can be esterified or etherified as illustrated in the following scheme.

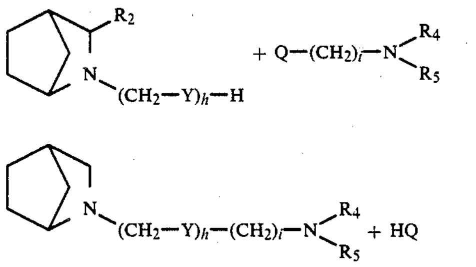

where:

h, i=equal or different: 2, 3 or 4

$R_2$, $R_4$, $R_5$=alkyl with 1 to 4 carbon atoms, preferably methyl

Y=O, acoxy, NH, or N-alkyl, preferably N-methyl

Q=halogen

By selecting different amines and varying functional groups in the side chain the properties of the 2-azabicyclo[2.2.1]heptane derivatives can be adjusted to the intended use.

The process of the invention for the preparation of these 2-azabicyclo[2.2.1]heptane derivatives allows to synthesize a variety of materials which have been unknown up to now and which, from the chemical viewpoint, come under the class of tertiary amines.

The expert knows that tertiary amines have many different uses. From the technical and economic point of view the plastics industry is a particularly important field of application for tertiary amines.

In this industry tertiary amines are used as reaction accelerators for crosslinking reactions. For this use, particularly for the polyurethane industry, the present invention provides novel types of catalysts which are a means for effectively matching new requirements. Such requirements may, for instance, arise from new application technologies, economics, industrial hygiene, production safety, environmental protection, etc.

As a result of their outstanding adaptability to varying applications, polyurethane plastics are widely used in industrial production. Furthermore, in the past decades the great variety of possible uses have resulted in the development of different production techniques tailored for the specific use.

Irrespective of the structure obtained, e.g., foams, microcelluloses, elastomers, adhesives, varnishes, etc., the polyurethane linkages are formed by polyols and polyfunctional isocyanates. Moreover, it is the state of the art to jointly use disparate auxiliaries, such as foam stabilizers, flame retardants, emulsifiers, etc. as required for the respective application.

Among the auxiliaries, catalysts play an important role. On the one hand, they accelerate formation of the urethane bond:

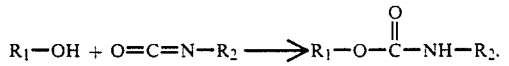

on the other hand, in foamed systems, as far as "water-blown foams" are considered, also the reaction of water and isocyanate is catalyzed. In this reaction carbon dioxide is generated in situ as a blowing gas:

$$H_2O+O{=}C{=}N-R \rightarrow CO_2+H_2N-R$$

It is the state of the art to use organometallic compounds of disparate chemical structures and tertiary amines as catalysts. Among the organometallic compounds, tin compounds (e.g., dibutyl tin (IV) dilaurate, tin (II) dioctoate as the best known materials) occupy a prominent position.

Whilst all the organometallic compounds are Lewis acids, tertiary amines are Lewis bases with likewise strong catalytic effects.

The expert knows that the joint use of Lewis acids and Lewis bases is usually characterized by synergistic effects. The use of such synergistically acting systems is very much dependent on the respective application.

It is also the state of the art that for many applications solely amines are used for catalysis.

In the relevant technical literature a great number of amines are suggested as catalysts (cf. Stanford Res. Report No. 10 A and 10B; Ullman, edition; Kunststoff-handbuch, Vol. VII; Polyurethanes, Hanser Verlag, Munchen, Wien 1983).

However, only relatively few amine structures have been accepted on a broader basis in the art. The expert knows such amine structures, e.g., 1,4-diazabicyclo[2.2.-1]octane, bis-(2-dimethylaminoethyl)ether, dimethlcyclohexylamine, dimethylethanolamine, dimethybenzylamine, methylmorpholine, ethylmorpholine, just to mention the most important.

In practice, the use of amine mixtures has often turned out to be favorable. In this connection also other, less customary amines, such as piperazine derivatives, alkylated fatty amines, and many others are recommended, as the expert knows.

Among the abovementioned catalyst types, those have been particularly accepted in the art which can be universally used, have a high activity, and can be economically produced on a large scale. It was surprisingly found that certain 2-azabicyclo[2.2.1]heptane derivatives are particularly suitable for this purpose.

These 2-azabicyclo[2.2.1]heptane derivatives can be produced on a large scale from inexpensive raw material.

It is particularly surprising that 2-azabicyclo [2.2.1]heptane catalysts have significantly higher activities than conventional monocyclic amine catalysts, while the C-number is the same. For instance, in applied formulations the efficiency of N-ethyl-2-azabicyclo[2.2.1]heptane is twice as high as that of N,N-dimethylcyclohexylamine.

It is another desirable effect of the catalysts of the invention that by selection of suitable substitutes on the nitrogen the activity of the products can be tailored according to the needs, whereas from the economic viewpoint, variation of 1,4-diazabicyclo[2.2.2]octane cannot be justified.

Thus, the N-methyl-2-azabicyclo[2.2.1]heptane brings about a three- to fourfold increase in activity as compared to dimethylcyclohexylamine. The n-butyl derivative has almost the same activity, but better levelling characteristics, e.g., in the production of rigid foam.

The synthesis of the invention offers the possibility of using a great number of disparate mono- and difunctional primary amines for the synthesis of the catalysts of the invention.

Using alkanol amines, such as monoethanolamine or 2-aminoethoxyethanol, for the preparation of the amine catalysts of the invention, N-(2-hydroxyethyl-)2-azabicyclo[2.2.1]heptane and N-(2-hydroxyethoxyethyl-)2-azabicyclo[2.2.1]heptane are formed.

The types of structure

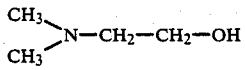 N,N-dimethylethanolamine and

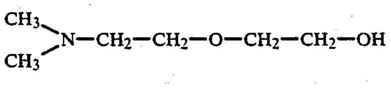 2-(2-Dimethylaminoethoxy-)ethanol are known as "incorporable amine catalysts" in the polyurethane sector, because the OH function can also be added to isocyanate.

It is surprising that the catalytic activity of the 2-azabicyclo[2.2.1]heptane derivatives prepared from alkanol amines is superior to that of the long-term alkanol amines N,N-dimethylaminoethanol and 2-(2 -dimethylamino ethoxy)ethanol.

In addition, further advantages can be observed, e.g., significantly lower volatility and, thus, considerably reduced odor nuisance during the manufacture of polyurethane products, good hardening, etc.

Other N-substituted 2-azabicyclo[2.2.1]heptane derivatives according to the invention are derived from diamines with, for instance, the following parent substances:

$N_2N-(CH_2)_n-NH_2$ where: n=2, 3, 4, etc. (ethylene diamine; 1, 3-diaminopropane etc.)

but also $H_2N-CH_2-CH_2-O-CH_2-CH_2-NH_2$ (Bisaminoethylether)

From the 2-azabicyclo[2.2.1]heptyl residue symmetric and asymmetric derivatives of the amine catalysts according to the invention can be prepared, depending on the synthesis conditions chosen, e.g.

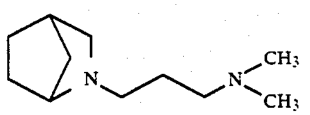

N-(3-dimethylaminopropyl-)2-azabicyclo[2.2.1]heptane

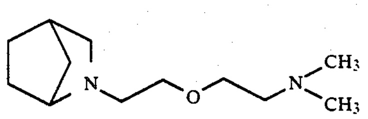

N-(2-dimethylaminoethoxyethyl-)2-azabicyclo[2.2.1-]heptane

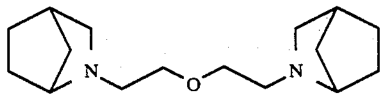

Bis-(2-azabicyclo[2.2.1]heptyl-ethyl-)ether

All of these compounds are characterized by very surprising effects. For instance, the activity of the compound

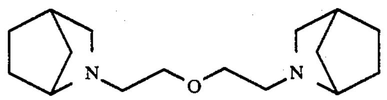

Bis-(2-azabicyclo[2.2.1]heptyl-ethyl)ether increases extraordinarily as compared to bis-(2-morpholino ethyl-)ether, such that cold mold foam (HR foam) can be produced with this material, the hardening taking place very rapidly.

On the other hand, as a result of its molecular weight and the cyclic substituents on the nitrogen, bis-(2-morpholinoethyl-)ether

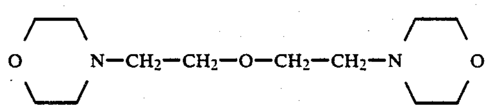

is a totally different catalyst type, as compared to bis-(2-azabicyclo[2.2.1]heptyl-ethyl-)ether. Bis-(2-morpholinoethyl-)ether does have a good activity for accelerating the water/isocyanate reaction (blowing reaction), but its gelating efficacy is only low.

Hence bis-(2-morpholinoethyl-)ether is a good blowing catalyst suitable for making polyester flexible foam, but due to its gelating efficacy, it is completely unsuitable for the production of polyether flexible foam (cold mold foam, HR foam).

Finally, it has to be mentioned that also the 2-azabicyclo[2.2.1]-hept-5-enes have catalytic activities according to the present invention. However, it is disadvantageous that these materials are very sensitive and quickly discolor under the influence of heat, light, and/or air (oxygen) and, finally, decompose which drastically confines their practical use.

The efficacy of the polyurethane catalysts suggested according to the invention shall be illustrated in the following examples:

EXAMPLE 1

COMPARISON CATALYSTS

For the production of polyurethane rigid foam, catalysts such as N,N-dimethylcyclohexylamine and also mixtures of 1,4-diazabicyclo[2.2.2]octane and N,N-dimethylaminoethanol are normally used. The expert knows that N, N-dimethylcyclohexylamine is a particularly dominant catalyst worldwide.

To demonstrate the state of the art, N,N-dimethylcyclohexylamine as well as a mixture of 1,4-diazabicyclo[2.2.2]octane and N,N-dimethylaminoethanol were chosen as comparison catalysts for a typical rigid foam formulation.

For preparing a rigid foam on a laboratory scale the following formulation was used:

TABLE 1

| | | | |
|---|---|---|---|
| Vorano ® 490 (1) | 33.13 g | 33.13 g | |
| Silicone DC ® 193(2) | 0.6 g | 0.6 g | |
| Water | 0.4 g | 0.4 g | |
| Trichlorofluoromethane | 16.3 g | 16.3 g | |
| Rubinate ® M(3) | 49.57 g | 49.57 g | |
| N,N-Dimethylcyclonexylamine (Comparison catalyst I) | 0.9 g | — | |
| 1,4-Diazabicyclo[2.2.2]octane | — | 0.16 g | 0.8 g |
| N,N-Dimethylaminoethanol (Comparison catalyst II) | — | 0.64 g | |
| Cream Time (s) | 18 | 20 | |
| Gel Time | 109 | 97 | |
| Tack free time (s) | 135 | 125 | |
| Rise time (s) | 157 | 150 | |
| Friability | None | None | |
| L-mold test, % fill | 82 | 79 | |

(1)Product from Dow Chemical, neutral polyol, OH number 490
(2)Product from Dow Corning
(3)Product from Rubicon Polymers MDI, functionality 2.7

EXAMPLE 2

To demonstrate the properties of the novel amine catalysts according to the invention in polyurethane rigid foam applications, the same formulation as in Example 1 was used, the difference being that, in addition, different 2-azabicyclo[2.2.1] heptane derivatives were used. The respective amine concentrations were chosen such that the foam rise times specified in Example I were met as well as possible:

TABLE 2

| Amine Catalyst (varied) | Amount (9) | Cream Time (s) | Gel Time (s) | Tack Free Time (s) | Rise Time (s) | Friability | L-Mold Test % Fill |
|---|---|---|---|---|---|---|---|
| Comp. Catalyst I | 0.9 | 18 | 109 | 135 | 157 | None | 82 |
| Comp. Catalyst II | 0.8 | 20 | 97 | 125 | 150 | None | 79 |
| N-Methyl-R | 0.5 | 19 | 85 | 107 | 145 | None | 82 |
| N-Ethyl-R | 0.5 | 16 | 107 | 134 | 151 | None | 87 |
| N-Isopropyl-R | 1.5 | 13 | 116 | 129 | 154 | Poor | 83 |
| N-Butyl-R | 0.8 | 16 | 93 | 109 | 147 | Moderate | 87 |
| N-Cyclohexyl-R | 2.0 | 14 | 122 | 112 | 170 | Poor | 87 |
| N-Methoxypropyl-R | 1.0 | 16 | 109 | 118 | 155 | Moderate | 79 |

R = 2-azabicyclo[2.2.1]heptane

Comparing the results in Table 2, the amine catalysts according to the invention give surprising results, as compared to conventional products.

A comparison of the catalysts N,N-dimethycyclohexylamine (Table 2, line 1, Example 2) and N-ethyl-2-azabicycloheptane (Table 2, line 4, Example 2) shows that—although these two materials contain the same amount of carbon atoms—N-ethyl-2-azabicyclo[2.2.1-]heptane is almost twice as active and has better levelling characteristics during foaming.

The L-mold fill in % of volume using the same quantity of the formulation is a means for measuring the flowability of the foam. The higher the mold fill in %, the better the flow and levelling properties attainable by he catalyst in the same formulation.

EXAMPLE 3

This example illustrates that the amine catalysts of the invention also bring about very surprising effects when used in spray foams.

Formulation 1 with N,N-dimethylcyclohexylamine as an amine catalyst in a spray foam formulation also used in practice.

Formulation 2 is the same spray foam formulation, but with N-ethyl-2-azabicyclo[2.2.1]heptane.

TABLE 3

| | Parts by Weight in Formulation | |
|---|---|---|
| | 1 | 2 |
| Thanol R 350 X(1) | 16.01 | 16.13 |
| Thanol R 470 X(2) | 6.40 | 6.45 |
| Thanol SF 265 X(3) | 1.60 | 1.61 |
| Terate 203(4) | 8.00 | 8.07 |
| Glycerine | 1.5 | 1.5 |
| Antiblaze 80(5) | 4.0 | 4.0 |
| DABCO LK 443(6) | 0.45 | 0.45 |
| Lead octoate (24%) | 0.035 | 0.035 |
| Trichlorofluoromethane | 11.5 | 11.5 |
| Rubinate M(7) | 49.5 | 50.0 |
| NCO Index | 118 | 117 |
| Amine Variation | | |
| N,N-Dimethylcyclohexylamine | 0.5 | — |
| N-Ethyl-2-azabicyclo[2.2.1] heptane | — | 0.25 |

(1)Amine basic polyol, OH number 530, product from Texaco Inc.
(2)Amine basic polyol, OH number 470, product from Texaco Inc.
(3)Amine basic reactive polyol, OH number 635, product from Texaco Inc.
(4)Aromatic polyestr polyol, product from Hercules
(5)Trichloropropylphosphat, product from Albright and Wilson, Inc.
(6)Non silicone surfactant, product from Air Products
(7)Polymer MDI, functionality 2.7, product from Rubicon The formulations 1 and 2 were foamed using a Gusmer FF apparatus, ARA (125) model, at a head temperature of 49° C.

TABLE 4

| | Formulation | |
|---|---|---|
| | 1 | 2 |
| Cream time, s | 1 | 1 |
| Tack free time, s | 7 | 7 |
| Rise time, s | 8 | 11 |
| Physical Properties | | |
| Foam density, kg/m³ | 40 | 43 |
| K-factor (btn × inch/ft² × h × F.°) | 0.114 | 0.115 |
| Friability, % weight loss | 0.28 | 0.13 |
| Heat distortion, °C. | 134 | 142 |
| Closed cells, % | 97.7 | 97.6 |

TABLE 4-continued

| | Formulation | |
|---|---|---|
| | 1 | 2 |
| Compressive strength, k Pa | | |
| parallel to foaming direction | 307 | 333 |
| perpendicular to foaming direction | 174 | 189 |

EXAMPLE 4

For the production of packaging foam those amine catalysts are customarily used in the art which have at least one OH function in the molecule. Thus, the amine is fixed in the foam and will not have any undesirable effects on the goods to be packaged.

For instance, a catalyst type commonly used in practice for this application is N,N-dimethylaminoethoxyethanol. In comparison with N,N-dimethylaminoethoxyethanol and N,N-dimethylaminoethanol as comparison catalysts, the materials N-(2-hydroxyethoxyethyl)-2-azabicyclo[2.2.1]heptane and N-hydroxyethyl-2-azabicyclo[2.2.1]heptane have the following reactivities:

TABLE 5

| | Parts by Weight in Formulation | | | |
|---|---|---|---|---|
| | 1 | 2 | 3 | 4 |
| Thanol SF 5505[(1)] | 45 | 45 | 45 | 45 |
| Thanol R 650 X[(2)] | 45 | 45 | 45 | 45 |
| Surfonic N 120[(3)] | 10 | 10 | 10 | 10 |
| Water | 40 | 40 | 40 | 40 |
| Silicon L 550[(4)] | 3.0 | 3.0 | 3.0 | 3.0 |
| Rubinate M[(5)] | 200 | 200 | 200 | 200 |
| NCO-Index | 31 | 31 | 31 | 31 |
| Amine (varied) | | | | |
| N-(2-Hydroxyethoxyethyl-) 2-azabicyclo[2.2.1]heptane | 2.3 | — | — | — |
| 2-(2-Dimethylaminoethoxy-) ethanol (Comparison catalyst) | — | 3.0 | — | — |
| N-(2-Hydroxyethyl)- 2-azabicyclo[2.2.1]heptane | — | — | 4.2 | — |
| N,N-Dimethylaminoethanol (Comparison catalyst) | — | — | — | 7.0 |
| Cream time (s) | 12 | 12 | 8 | 14 |
| Gel time (s) | 28 | 31 | 28 | 30 |
| Tack free time (s) | 36 | 40 | 40 | 37 |
| Rise time (s) | 35 | 38 | 38 | 37 |
| Density (kg/m$^3$) | 9.6 | 9.0 | — | — |

(1)Polymer polyol, OH-number 32-36 mg KOH/g, product from Texaco Inc.
(2)Aminopolyol, OH-number 450 mg KOH/g, product from Texaco Inc.
(3)Nonionic surfactant, OH-number 75
(4)Silicone surfactant, product from Union Carbide
(5)Polymer MDI, functionality 2.7 product from Rubicon The results of the formulations 1 and 3 in Example 4 show that despite their higher molecular weight the 2-azabicyclo[2.2.1]heptane derivatives used in significantly lower amounts have the same efficacy as the corresponding methylated alkanol amines used in the formulations 2 and 4.

EXAMPLE 5

Instrument panel foam is another important field of application for polyurethane plastics. Products of this type consist of a foam body (with or without supporting reinforcement of metal, plastics, or any other material) plus a decorative foil covering the visible part of the product.

Normally, PVC foils are used in foaming applications. However, PVC foils are very sensitive to amines. The expert knows that particularly those amines which are not chemically incorporated in the product after the foaming reaction is complete (such as 1,4-diazabicyclo[2.2.2]octane, trimethylaminoethylpiperazine, etc.) result in particularly strong discoloration of the vinyl top coat. The experts are interested in materials belonging to the alkanol amine group.

Optimization of the performance of foam formulations is usually preceded by tests examining in particular the tendency to discoloration of any amine catalyst in contact with PVC foils.

Example 5 describes such a selective examination for which the following amine catalysts were used:

A. N-(2-Hydroxyethyl-)2-azabicyclo[2.2.1]heptane (catalyst according to the invention)

B. 1-N,N-Dimethylamino-3-N', N'-bis-(2-hydroxypropyl-)aminopropane (commercially available comparison catalyst)

C. N,N,N'-Trimethylaminoethylethanolamine (commercially available comparison catalyst)

D. N,N,N'-Trimethylaminopropylethanolamine (commercially available comparison catalyst)

E. 1-(Bis-3-dimethylaminopropyl-)aminopropan-2-ol (commercially available comparison catalyst)

F. Dimethylaminoethanol (commercially available comparison catalyst).

At first foam specimens were prepared in beakers in order to detect similar reaction times, if any.

The following formulation was used for this preparation:

TABLE 6

| | Parts by Weight in Formulation | | | | | |
|---|---|---|---|---|---|---|
| | 1 | 2 | 3 | 4 | 5 | 6 |
| Thanol SF 3950[(1)] | 97.4 | 97.4 | 97.4 | 97.4 | 97.4 | 97.4 |
| Soot[(2)] | 2.0 | 2.0 | 2.0 | 2.0 | 2.0 | 2.0 |
| Formrez II-225[(3)] | 2.4 | 2.4 | 2.4 | 2.4 | 2.4 | 2.4 |
| Niax 50-970[(4)] | 6.0 | 6.0 | 6.0 | 6.0 | 6.0 | 6.0 |
| Water | 2.2 | 2.2 | 2.2 | 2.2 | 2.2 | 2.2 |
| Rubinate M[(5)] | 51.0 | 51.0 | 51.0 | 51.0 | 51.0 | 51.0 |
| Amine (varied) | | | | | | |
| A (Catalyst or the invention) | 0.76 | — | — | — | — | — |
| B (Comparison catalyst 1) | — | 1.2 | — | — | — | — |
| C (Comparison catalyst 2) | — | — | 0.5 | — | — | — |
| D (Comparison catalyst 3) | — | — | — | 0.64 | — | — |
| E (Comparison catalyst 4) | — | — | — | — | 0.56 | — |
| F (Comparison catalyst 5) | — | — | — | — | — | 0.86 |
| Rise time, s | 81 | 74 | 76 | 85 | 81 | 83 |
| Gel time, s | 260 | 215 | 210 | 240 | 225 | 260 |

(1)Polymer polyol, OH number 30 mg/KOH, product from Texaco Inc.
(2)8% soot dissolved in polyol
(3)Formrez II-225, Polyester polyol, product from Nitco
(4)Niax 50-970, Polyether polyol, product from Union Carbide Corp.
(5)Polymer-MDI, functionality 2.7, product from Rubicon In a rectangular mold (about 8×8 cm, side height about 2 cm) foil-coated specimens were then foamed. To this end a red PVC foil (Davidson Rubber) was placed in the mold, the material was allowed to foam, and the foam specimen was demolded after 6 minutes. From these foam cubes specimens of 5×5 cm size were cut and subsequently aged during 48 hours at 121° C. (250° F.).

By visual inspection of the specimens with respect to discoloration the following was found:

TABLE 7

| Catalyst | | Discoloration of the Foil |
|---|---|---|
| A | (according to invention) | no detectable discoloration |
| B | | about 50% discoloration |
| C | | about 50% discoloration |
| D | | complete discoloration |
| E | | about 70-80% discoloration |
| F | | about 10-20% discoloration |

As demonstrated by Example 5, surprisingly no discoloration of the PVC foil was found when using the catalyst of the invention, N-(2-hydroxyethyl-)2-azabicyclo[2.2.1]heptane, in contrast to other catalysts.

EXAMPLE 6

The following example illustrates the use of bis-(2-azabicyclo[2.2.1]heptyl-ethyl)ether in comparison with bis-(2-dimethylaminoethyl-)ether in flexible cold mold foams.

TABLE 8

| | Parts by Weight in Formulation | |
|---|---|---|
| | 1 | 2 |
| Thanol SF 5505[(1)] | 60 | 60 |
| Niax 34-28[(2)] | 40 | 40 |
| Silicone L 5309[(3)] | 1.5 | 1.5 |
| Diethanolamine | 1.5 | 1.5 |
| Water | 3.5 | 3.5 |
| Didecylthiodibutyltin | 0.06 | 0.06 |
| Bis-(2-dimethylaminoethyl-)ether[(4)] | 0.3 | — |
| Dipropylene glycol | 0.13 | — |
| Bis-(2-azabicyclo[2.2.1]heptyl-ethyl-)ether | | 0.6 |
| Toluene diisocyanate | 43.3 | 43.3 |
| NCO/OH Index | 102 | 102 |
| Cream time (s) | 5 | 5 |
| Rise time (s) | 63 | 61 |

(1)Thanol SF 5505, polyether polyol, OH number 33 mg KOH/g, product from Texaco Inc.
(2)Niax 34-28, styrene/acrylonitrile polymer polyol, OH number 28 mg KOH/g, product from Union Carbide Corp.
(3)Product from Union Carbide Corp.
(4)Product from Texaco Inc.

The gelatin (% gel content in the foam dependent on time) determined to the falling-sphere test (Texaco Method, R. L. Rowton, J. Cell. Plast., 16(5), 287–292) was found to be as follows:

TABLE 9

| Rise Time of the Foam in | % Gel Content in Formulation | |
|---|---|---|
| s | 1 | 2 |
| 20 | 0 | 0 |
| 25 | 0 | 18 |
| 30 | 0 | 70 |
| 35 | 53 | 90 |
| 40 | 92 | 94 |
| 45 | — | 96 |
| 50 | 96 | 97 |
| 55 | 97 | 97 |
| 60 | 97 | 98 |

The results indicate that formulation 2 using a catalyst amine of the invention is superior by a rapid formulation of the polymer structure. In practice this effect is mostly attained by adding to the blowing catalyst. bis-(2-dimethylaminoethyl-)ether in formulation 1, catalysts that prop the gelation reaction, normally 1,4-diazabicyclo-[2.2.1]ocatane.

Foams prepared in the laboratory according to Example 6, formulation 1, had an amine odor, but not so had the foams prepared according to formulation 2.

EXAMPLES

The general operating instructions for the preparation of 2-azabicyclo[2.2.1]hept-5-ene derivatives are provided below for Variants A, B, C and D which include the various examples.

VARIANT A (Starting From Free Amine)

5 moles of the amine are neutralized with concentrated hydrochloric acid or 50% sulfuric acid. After addition of 5 moles or aqueous formalin solution the pH value is adjusted to 2.5. The immonium salt solution is heated at 40° C. and 5.5 moles (363.6 g) or cyclopentadiene are added such that the reaction mixture is kept boiling, the temperature inside the reaction rising from 40° C. at the beginning to about 45° C. at the end of reaction. When the addition of cyclopentadiene is complete, stirring is continued for one hour without addition of heat.

Excess cyclopentadiene (partly as dicyclopentadiene) is then separated as the upper phase. 5.25 moles (420 g) of 50% sodium hydroxide solution is added to the water phase in which the 2-azabicyclo[2.2.1]hept-5-ene derivative is dissolved as a salt, the free bases being separated. With readily water-soluble compounds, e.g., 2-methyl-2-azabicyclo[2.2.1]hept-5-ene, the water phase has to be saturated with NaOH or KOH.

The crude product is dried by addition of solid NaOH or KOH and is distilled under vacuum.

VARIANT B (Starting From Ammonium Salt)

This procedure is particularly suitable for the preparation of readily water-soluble 2-azabicyclo[2.2.1]hept-5-ene derivatives. 5 moles of aqueous formaldehyde solution are added to 5 moles of the ammonium salt, e.g., chloride, sulfate, or phosphate, while stirring vigorously. When the pH value is adjusted to 2.5, proceed as described sub Variant A.

EXAMPLE 1

N-Methyl-2-Azabicyclo[2.2.1]Hept-5-ene (I)

According to Variant A, 443.7 g (5 moles) of a 35% solution of methyl amine in water are reacted. After vacuum distillation 468 g of (I) having a purity of 99% are obtained from 712 g of aqueous crude product containing 67.5% (I). This corresponds to a yield of 83% of theoretical.

EXAMPLE 2

N-Methyl-2-Azabicyclo[2.2.1]Hept-5-ene (I)

337.6 g of methylammonium chloride are reacted according to Variant B and are worked up. After vacuum distillation 494 g of (I) having a purity of 98.5% are obtained. This corresponds to a yield of 87.5% of theoretical.

EXAMPLE 3

N-Ethyl-2-Azabicyclo[2.2.1]Hept-5-ene (II)

According to Variant A, 322 g 5 moles of a 70% solution of ethylamine in water are reacted and worked up. After vacuum distillation 575 g of (II) having a purity of 99% are obtained. This corresponds to a yield of 91% of theoretical.

EXAMPLE 4

N-N-Propyl-2-Azabicyclo[2.2.1]Hept-5-ene (III)

By reacting 298 g (5 moles) of n-propylamine according to Variant A 570 g of a product containing 98%

(III) are obtained. This corresponds to a yield of 80% of theoretical.

EXAMPLE 5

N-I-propyl-2-Azabicyclo[2.2.1]Hept-5-ene (IV)

295 G (5 moles) of isopropylamine are reacted according to Variant A. After vacuum distillation 626 g of (IV) having a purity of 97% are obtained. This corresponds to a yield of 87% of theoretical.

EXAMPLE 6

N-allyl-2-Azabicyclo[2.2.1]Hept-5-ene (V)

According to Variant A, 144 g (2.5 moles) of allyl amine are neutralized with hydrochloric acid solution, are reacted with 187.5 g (2.5 moles) of 40% formalin solution and 198 g (3.0 moles) of cyclopentadiene, and are worked up. After vacuum distillation 313 g of a product containing 98% (V) are obtained. This corresponds to a yield of 91% of theoretical.

EXAMPLE 7

N-butyl-2-Azabicyclo[2.2.1]Hept-5-ene (IV)

By reacting 365.7 g (5 moles) of n-butylamine according to Variant A 686 g of product containing 98% (VI) are obtained after working up. This corresponds to a yield of 89% of theoretical.

General operating instructions for the preparation of 2-azabicyclo[2.2.1]heptane derivatives.

VARIANT C

According to Variant A, 5 moles of amine are reacted with formalin and cyclopentadiene. To lower the water and salt content, the crude product is worked up as follows:

250 g of cyclohexane and 5.25 moles (420 g) of 50% sodium hydroxide solution are added to the acidic reaction product freed from unreacted cyclopentadiene. Separation into phases is achieved at about 40° C., the upper phase being hydrogenated at elevated pressure after addition of a commercially available supported palladium catalyst with 5% Pd (e.g. 5% Pd supported on carbon). The catalyst is filtered off after hydrogenation. After azeotropic drying of the hydrogenation product—the cyclohexane acting as a water entrainer—the 2-azabicyclo[2.2.1]heptane is obtained by distillation.

VARIANT D According to Variant A, readily water-soluble, high-boiling amines are reacted. After separation of unreacted cyclopentadiene, 200 g of n-butanol and 5.25 moles (420 g) of 50% sodium hydroxide solution are added to the acidic reaction mixture. Separation into phases and hydrogenation are performed as described sub Variant C. The hydrogenation product is azeotropically dried, while utilizing n-butanol/water azeotrope, and is subsequently distilled under vacuum.

EXAMPLE 8

N-methyl-2-Azabicyclo[2.2.1]Heptane (VII)

The preparation of (VII) starts from 388 g (5 moles) of a 40% solution of methylamine in water and is performed according to Variant C. By distillation under atmospheric pressure 406 g of product containing 99% (VII) are obtained. This corresponds to a yield of 72 % theoretical. Boiling point: 134° C./1013 mbar; $n_D20°$:1.4645

EXAMPLE 9

N-ethyl-2-Azabicyclo[2.2.1]Heptane(VIII)

According to Variant C, 322 g (5 moles) of a 70% solution of ethylamine in water are reacted. After vacuum distillation 463 g of product containing 98.5% (VIII) are obtained. This corresponds to a yield of 73% theoretical. Boiling point: 64°-65° C./27 mbar; $n_D20°$:1.4636

EXAMPLE 10

N-(2-hydroxyethyl-)2-Azabicyclo[2.2.1]Heptane (IX)

According to Variant D, 306 g (5 moles of monoethanolamine are reacted. By vacuum distillation 562 g of a viscous product containing 98% (IX) are obtained. This corresponds to a yield of 78% of theoretical.

EXAMPLE 11

N-propyl-2-Azabicyclo[2.2.1]hehptane (X)

According to Variant C, 296 g (5 moles) of n-propylamine are reacted. After vacuum distillation 575 g of product containing 98% (X) are obtained. This corresponds to a yield of 81% of theoretical.

EXAMPLE 12

N-i-propyl-2-Azabicyclo[2.2.1]Heptane (XI)

According to Variant C, 296 g (5 moles) of isopropylamine are reacted. After vacuum distillation 580 g of product containing 99% (XI) are obtained. This corresponds to a yield of 82% of theoretical. Boiling point: 71.5° C./25 mbar; $n_D20°$:1.4651

EXAMPLE 13

N-(3-methoxypropyl-)2-Azabicyclo 2.2.1 Heptane (XII) 455g (5 moles) of 3-methoxypropylamine are reacted according to Variant C. The distillate weighs 624 g and contains 99% (XII). This corresponds to a yield of 73% of theoretical.

EXAMPLE 14

N-n-butyl-2-Azabicyclo[2.2.1]Heptane (XIII)

According to Variant C, 366 g (5 moles) of n-butyl amine are reacted. After vacuum distillation 700 g of product containing 98.5% (XIII) are obtained. This corresponds to a yield of 90% of theoretical.

EXAMPLE 15

N-(2-ethylhexyl-)2-Azabicyclo[2.2.1]Heptane (XIV)

According to Variant C, 645 g (5 moles) of 2-ethylamine are reacted. After vacuum distillation 897 g of product containing 98% (XIV) are obtained. This corresponds to a yield of 84% of theoretical.

EXAMPLE 16

N-(2-hydroxyethoxyethyl-)2-Azabicyclo[2.2.1]Heptane (XV)

According to Variant D, 525 g (5 moles) of diglcol amine are reacted. After vacuum distillation 646 g of a viscous liquid containing 97.5% (XV) are isolated. This corresponds to a yield of 68% of theoretical.

EXAMPLE 17

N-cyclohexyl-2-Azabicyclo[2.2.1]Heptane (XVI)

According to Variant C, 496 g (5 moles) of cyclohexylamine are reacted. After vacuum distillation 760 g of product containing 99% (XVI) are obtained. This corresponds to a yield of 84% of theoretical.

EXAMPLE 18

N-bencyl-2-Azabicyclo[2.2.1]Heptane (XVII)

According to Variant C, 536 g (5 moles) of bencyl amine are reacted. After vacuum distillation 846 g of product containing 98.5% (XVII) are obtained. This corresponds to a yield of 89% of theoretical.

EXAMPLE 19

Bis-(2-Azabicyclo[2.2.1]Heptyl-)ethylether (XVIII)

According to Variant D, 520 g (5 moles) of bisaminodiethylether are reacted. After vacuum distillation 1,200 g of product containing 98% (XVIII) are obtained. This corresponds to a yield of 89% of theoretical.

EXAMPLE 20

N-(2-hydroxypropyl-)2-Azabicyclo[2.2.1]Heptane (XIX)

According to Variant D, 950 g (12 moles) of 1-amino-2-propanol are reacted. After vacuum distillation 817 g of a viscous liquid containing 96.5% (XIX) are obtained. This corresponds to a yield of 50% of theoretical.

EXAMPLE 21

N-(3-dimethylaminopropyl-)2-Azabicyclo[2.2.1]Heptane (XX)

According to Variant D, 511 g (5 moles) of dimethylaminopropylamine are reacted. After vacuum distillation 103 g of a yellowish liquid containing 97% (XX) are obtained. This corresponds to a yield of 11% of theoretical. From the residue a section fraction weighing 187 g (b.p. 142°-146° C./25 mbar) can be isolated. In this fraction three components were detected by GC-analysis.

Variation of 2-Azabicyclo[2.2.1]Heptane Derivatives
Esterification

EXAMPLE 22

N-(2-Acetoxyethoxyethyl-)2-Azabicyclo[2.2.1]Heptane (XXI)

198 g (1.94 moles) of acetic anhydride are added to 286 g (1.55 moles) of N-(2-hydroxyethoxyethyl-)2-azabicyclo[2.2.1]heptane (XV) in the absence of moisture such that the temperature is maintained between 50° and 60° C. The mixture is kept boiling for three hours. After cooling 200 ml of ether are added. The product is neutralized with soda solution, is washed until it is neutral, and—after the ether is withdrawn—it is distilled under high vacuum. The main fraction weighs 185 g and contains 99% (XXI). This corresponds to a yield of 52% of theoretical.

Estherification

EXAMPLE 23

N-(2-Dimethylaminoethoxtethyl-)2-Azabicyclo[2.2.1-]Heptane (XXII)

80 g (2.0 moles) of NaOH are added to 384 g (2.7 moles) of N-(2-hydroxyethyl-)2-azabicyclo[2.2.1]heptane (IX) and heated at 105° C. while stirring. Within 30 minutes a fresh solution of 1-chloro-2-dimethylaminoethane in about 250 ml of toluene (starting from 288 g (2.0 moles) of hydrochloride and 240 g of 50% sodium hydroxide solution) is added while stirring vigorously. After heating at reflux temperature for six hours, the product is cooled at room temperature, and precipitated NaCl is filtered off. After washing twice with toluene, the solvent is removed and the product is distilled under vacuum using a 40-cm packed column. 150 g of main fraction containing 99.5% (XXII) are obtained. This corresponds to a yield of 35% of theoretical, relative to 1-chloro-2-dimethylaminoethanehydrochloride used.

TABLE 10

Physical Properties of the New Compounds
According to Formula A

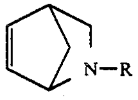

| Product | R | $n_D20°$ | b.p./T |
|---|---|---|---|
| I | $CH_3$* | 1.4744 | 67 mbar/49° C. |
| II | $CH_2-CH_3$ | 1.4728 | 20 mbar/50° C. |
| III | $CH_2-CH_2-CH_3$ | 1.4720 | 27 mbar/70° C. |
| IV | $CH_3$<br>$CH_2$<br>$CH_3$ | 1.4724 | 20 mbar/53° C. |
| V | $CH=CH-CH_3$ | 1.4869 | 20 mbar/45° C. |
| VI | $CH_2-CH_2-CH_2-CH_3$ | 1.4714 | 11 mbar/68° C. |

*Described by S. D. Larsen and P. A. Grieco, J. Am Chem. Soc. 107, 1768 (1985), but without listing the physical data.

TABLE 11

Physical Properties of the New Compounds
According to Formula B

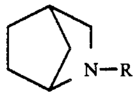

| Product | R | $n_D20°$ | b.p./T |
|---|---|---|---|
| IX | $CH_2-CH_2-OH$ | 1.4967 | 22 mbar/109° C. |
| X | $CH_2-CH_2-CH_3$ | 1.4635 | 27 mbar/70° C. |
| XII | $CH_2-CH_2-CH_2-O-CH_3$ | 1.4674 | 20 mbar/99° C. |
| XIII | $CH_2-CH_2-CH_2-CH_3$ | 1.4642 | 27 mbar/87° C. |
| XIV | $CH_2-CH-CH_2-CH_2-CH_2-CH_3$<br>$C_2H_5$ | 1.4654 | 3 mbar/103° C. |
| XV | $CH_2-CH_2-CCH_2-CH_2-OH$ | 1.4905 | 0.1 mbar/101-102° C. |

TABLE 11-continued

Physical Properties of the New Compounds According to Formula B

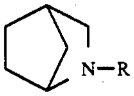

| Product | R | $n_D20°$ | b.p./T |
|---|---|---|---|
| XVI | 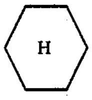 | 1.5005 | 20 mbar/121-122° C. |
| XVII | $CH_2$— 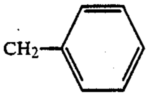 | 1.5401 | 20 mbar/140° C. |
| XVIII | $CH_2—CH_2—CCH_2—CH_2—$ 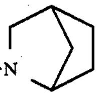 | 1.5030 | 0.9 mbar/143° C. |
| XIX | $CH_2—CH(OH)—CH_3$ | 1.4790 | 27 mbar/102-103° C. |
| XX | $CH_2—CH_2—CH_2—N(CH_3)_2$ | 1.4730 | 25 mbar/112° C. |
| XXI | $CH_2—CH_2—O—CH_2—CH_2—O—AC$ | 1.4770 | 0.2 mbar/107-110° C. |
| XXII | $CH_2—CH_2—O—CH_2—CH_2—N(CH_3)_2$ | 1.4731 | 20 mbar/139° C. |

We claim:

1. In a process for producing polyurethanes by reacting a polyol with a diisocyanate in the presence of a catalyst, the improvement comprising carrying out the reaction in the presence of a catalyst comprising:

substituted 2-aza-bicyclo[2.2.1]hept-5-ene derivatives of the formula

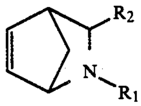

and of the corresponding 2-azabicycloheptane derivatives of the formula

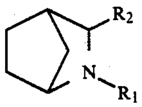

wherein $R_1$ is a ($C_1$-$C_8$) alkyl group, a ($C_2$-$C_8$) alkenyl group, a ($C_5$-$C_9$) cycloalkyl or alkylcycloalkyl group, benzyl or a ($C_3$-$C_{10}$) alkylbenzyl group with one or more of the heteroatoms N, O or S;

$—(CH_2)_a—P$, $—(CH_2)_b—T—(CH_2)_c—U$, or $—(CH_2)_d—V—(CH_2)_e—W—(CH_2)_f—X$;

wherein a through f are 2, 3 or 4;

P, U, X are each the same or different and are OH, O-acyl, N-acyl, N-($C_1$-$C_4$) alkyl, N-di(C-$_1$-$C_4$) alkyl, or are 2-azibicyclo-heptyl;

T, V, W are each equal or different and are O, NH, or N-($C_1$-$C_4$) alkyl and $R_2$ is hydrogen or a ($C_1$-C-4) alkyl group.

2. A catalyst as defined in claim 1 wherein $R_1$ is a $C_1$-$C_8$ alkyl group.

3. A catalyst according to claim 1 wherein $R_1$ is a $C_1$-$C_8$ alkenyl group.

4. A catalyst according to claim 1 wherein $R_1$ is a $C_5$-$C_9$ cycloalkyl or alkycycloalkyl group.

5. A catalyst according to claim I wherein $R_1$ is benzyl or $C_3$-$C_{10}$ alkylbenzyl group with one or more of the heteroatoms N, O or S.

6. A catalyst according to claim 1 wherein $R_1$ is a $—(CH_2)_a—F$ group.

7. A catalyst according to claim 1 wherein $R_1$ is a $—(CH_2)_b—T(CH_2)_c—U$ group.

8. A catalyst as defined in claim 1 wherein $R_1$ is a $—(CH_2)_d—U—(CH_2)_e—W—(CH_2)_f—X$ group.

9. A catalyst according to claim 1 comprising N-Ethyl-2-azabicyclo[2.2.1]hept-5-ene.

10. A catalyst according to claim 1 comprising N-Propyl-2-azabicyclo[2.2.1]hept-5-ene.

11. A catalyst according to claim 1 comprising N-i-Propyl-2-azabicyclo[2.2.19 hept-5-ene.

12. A catalyst according to claim 1 comprising N-Allyl-2-azabicyclo[2.2.1]hept-5-ene.

13. A catalyst according to claim 1 comprising N-Butyl-2-azabicyclo[2.2.1]hept-5-ene.

14. A catalyst according to claim 1 comprising N-(2-Hydroxyethyl-)2-azabicyclo[2.2.1]heptane.

15. A catalyst according to claim 1 comprising N-Propyl-2-azabicyclo[2.2.1]heptane.

16. A catalyst according to claim 1 comprising N-(3-Methoxypropyl)2-azabicyclo[2.2.1]heptane.

17. A catalyst according to claim 1 comprising N-Butyl-2-azabicyclo[2.2.1]heptane.

18. A catalyst according to claim 1 comprising N-(2-ethylhexyl-)2-azabicyclo[2.2.1]heptane.

19. A catalyst according to claim 1 comprising N-(2-Hydroxyethoxyethyl-)2-azabicyclo[2.2.1]heptane.

20. A catalyst according to claim 1 comprising N-Cyclohexyl-2-azabicyclo[2.2.1]heptane.

21. A catalyst according to claim 1 comprising N-Benzyl-2-azabicyclo[2.2.1]heptane.

22. A catalyst according to claim 1 comprising Bis-(2-azabicyclo[2.2.1]heptyl-ethyl-)ether.

23. A catalyst according to claim 1 comprising N-(3-Dimethylaminopropyl-)2-azabicyclo[2.2.1]heptane.

24. A catalyst according to claim 1 comprising N-(2-Acetoxyethoxyethyl-)2-azabicyclo[2.2.1]heptane.

25. A catalyst according to claim I comprising N-(2-Dimethylaminoethanoxethyl-)2-azabicyclo[2.2.1]heptane.

* * * * *